(12) United States Patent
Ali et al.

(10) Patent No.: US 8,377,911 B2
(45) Date of Patent: Feb. 19, 2013

(54) DIURETICS

(75) Inventors: Amjad Ali, Freehold, NJ (US); Michael Man-Chu Lo, Edison, NJ (US); Lin Yan, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/500,509

(22) PCT Filed: Sep. 20, 2010

(86) PCT No.: PCT/US2010/049425
§ 371 (c)(1),
(2), (4) Date: Apr. 5, 2012

(87) PCT Pub. No.: WO2011/043914
PCT Pub. Date: Apr. 14, 2011

(65) Prior Publication Data
US 2012/0202845 A1    Aug. 9, 2012

Related U.S. Application Data

(60) Provisional application No. 61/250,046, filed on Oct. 9, 2009.

(51) Int. Cl.
*A61K 31/655* (2006.01)
*C07D 471/06* (2006.01)

(52) U.S. Cl. .................. 514/149; 514/869; 534/556

(58) Field of Classification Search ........................ None
See application file for complete search history.

(56) References Cited

U.S. PATENT DOCUMENTS

| | | |
|---|---|---|
| 5,026,855 A | 6/1991 | Bonato |
| 5,910,316 A | 6/1999 | Keefer et al. |
| 6,949,530 B2 * | 9/2005 | Hrabie et al. .................. 514/149 |
| 2001/0031770 A1 | 10/2001 | Haque |

* cited by examiner

*Primary Examiner* — Fiona T Powers
(74) *Attorney, Agent, or Firm* — Richard S. Parr; Catherine D. Fitch

(57) ABSTRACT

A compound having the structure formula (I) or a pharmaceutically acceptable salt thereof, and methods of using the compounds for treating hypertension.

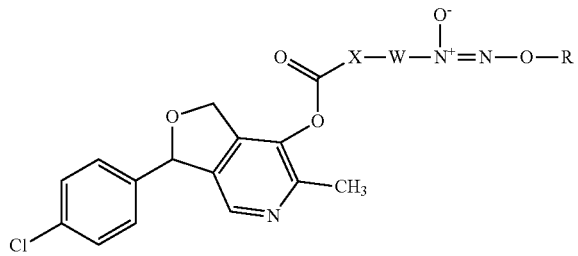

(I)

8 Claims, No Drawings

DIURETICS

BACKGROUND OF THE INVENTION

US 2005/0059655 describes nitrosated and nitrosylated furosemide derivatives (examples 1-16) having one or two nitroxy groups attached. The compounds are described as useful for treating conditions resulting from excessive water retention, cardiovascular disease, diabetes, oxidative stress, endothelial dysfunction, cirrhosis, pre-eclampsia, osteoporosis, and nephropathy.

U.S. Pat. No. 4,383,998 generically claims cicletanine. U.S. Pat. No. 5,026,855 claims the (+) enantiomer of cicletanine and compositions comprising the (+) enantiomer, and methods of preparation.

SUMMARY OF THE INVENTION

The present invention includes nitric oxide linked cicletanine, and derivatives thereof, including various pharmaceutically acceptable salts and hydrates of these forms, and pharmaceutical formulations for controlled and sustained delivery of these forms to a patient. The salts include non-toxic salts such as those derived from inorganic acids, e.g. hydrochloric, hydrobromic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

Compounds of the invention have the general formula I:

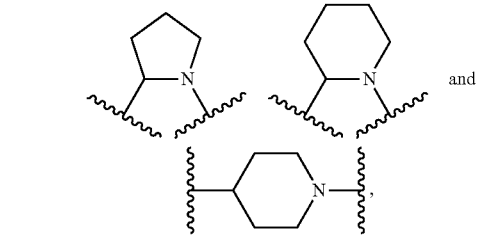

wherein
X is a bond or —O—$C_{1-6}$alkylene-, wherein $C_{1-6}$ alkylene is unsubstituted, mono-substituted at any carbon with $C_{1-6}$ alkyl, or independently disubstituted at different carbons with $C_{1-6}$ alkyl;
W is selected from the group consisting of

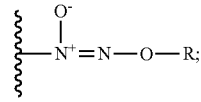

wherein N is attached to $$\text{―}N^+=N\text{―}O\text{―}R;$$
$$|$$
$$O^-$$

and
R is selected form the group consisting of $C_{1-6}$ alkyl and $C_{3-6}$ cycloalkyl.

In one embodiment of the invention, X is a bond or —OCH$_2$—.

In another embodiment, R is selected from the group consisting of methyl, ethyl, propyl, isopropyl, 2-methylpropyl, butyl, 3-methylbutyl, pentyl and pentan-2-yl.

In another embodiment of the invention, the compound is selected from the group consisting of
(3S)-3-(4-Chlorophenyl)-6-methyl-1,3-dihydrofuro[3,4-c] pyridin-7-yl 1-[(Z)-butoxy-NNO-azoxy]-L-prolinate,
(3S)-3-(4-Chlorophenyl)-6-methyl-1,3-dihydrofuro[3,4-c] pyridin-7-yl 1-[(2)-methoxy-NNO-azoxy]-L-prolinate,
(3S)-3-(4-Chlorophenyl)-6-methyl-1,3-dihydrofuro[3,4-c] pyridin-7-yl 1-[(Z)-ethoxy-NNO-azoxy]-L-prolinate,
(3S)-3-(4-Chlorophenyl)-6-methyl-1,3-dihydrofuro[3,4-c] pyridin-7-yl 1-[(Z)-isopropyloxy-NNO-azoxy]-L-prolinate,
(3S)-3-(4-Chlorophenyl)-6-methyl-1,3-dihydrofuro[3,4-c] pyridin-7-yl 1-[(Z)-2-methylpropoxy-NNO-azoxy]-L-prolinate,
(3S)-3-(4-Chlorophenyl)-6-methyl-1,3-dihydrofuro[3,4-c] pyridin-7-yl 1-[(Z)-propoxy-NNO-azoxy]-L-prolinate,
(3S)-3-(4-Chlorophenyl)-6-methyl-1,3-dihydrofuro[3,4-e] pyridin-7-yl 1-[(2)-pentoxy-NNO-azoxy]-L-prolinate, (3S)-3-(4-Chlorophenyl)-6-methyl-1,3-dihydrofuro[3,4-c]
   pyridin-7-yl 1-[(Z)-3-methylbutoxy-NNO-azoxy]-L-pro-
   linate,
(3S)-3-(4-Chlorophenyl)-6-methyl-1,3-dihydrofuro[3,4-c]
   pyridin-7-yl 1-[(Z)-pentan-2-yloxy-NNO-azoxy]-L-proli-
   nate,
(3S)-3-(4-Chlorophenyl)-6-methyl-1,3-dihydrofuro[3,4-c]
   pyridin-7-yl 1-((Z)-{[(2S)-2-methylbutyl]oxy}-NNO-
   azoxy)-L-prolinate,
(3S)-3-(4-Chlorophenyl)-6-methyl-1,3-dihydrofuro[3,4-c]
   pyridin-7-yl 1-[(Z)-cyclohexyloxy-NNO-azoxy]-L-proli-
   nate,
(3S)-3-(4-Chlorophenyl)-6-methyl-1,3-dihydrofuro[3,4-c]
   pyridin-7-yl 1-[(2)-butoxy-NNO-azoxy]piperidine-4-car-
   boxylate,
{(2S)-1-[(E)-butoxy-NNO-azoxy]pyrrolidin-2-yl}methyl
   (3S)-3-(4-chlorophenyl)-6-methyl-1,3-dihydrofuro[3,4-c]
   pyridin-7-yl carbonate, and
(3S)-3-(4-chlorophenyl)-6-methyl-1,3-dihydrofuro[3,4-c]
   pyridin-7-yl 1-[(E)-(cyclohexyloxy)-NNO-azoxy]piperi-
   dine-2-carboxylate
or a pharmaceutically acceptable salt thereof.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group, e.g. "ξ—", ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes n-, iso-, sec- and t-butyl, n- and isopropyl, ethyl and methyl. If no number is specified, 1-6 carbon atoms are intended for linear or branched alkyl groups. Unless otherwise specified, alkyl groups can be unsubstituted or mono- or di-substituted at any carbon atom with halogen, C$_{1-6}$ alkyl, and —O—C$_{1-6}$ alkyl. "Cycloalkyl" groups are alkyl groups, as defined above, having the specified number of carbon atoms that form a cyclic ring of that number of carbon atoms, such as cyclopropyl, cyclobutyl, cyclopentyl and cyclohexyl, and which can be unsubstituted or mono- or di-substituted at any carbon atom with halogen, C$_{1-6}$ alkyl, and —O—C$_{1-6}$ alkyl.

The diuretics of the invention are useful for treating hypertension, Pulmonary Arterial Hypertension, congestive heart failure, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of diuretics of the invention for the preparation of a medicament for the treatment and/or prophylaxis of the above-mentioned diseases.

The above-mentioned diuretics of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy)phenyl]-oetanamid hemifumarate) SPP600, SPP630 and SPP635), endothelin receptors antagonists, vasodilators, calcium channel blockers (e.g., amlodipine, nifedipine, veraparmil, diltiazem, gallopamil, nifedipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

The dosage regimen utilizing the diuretics is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the diuretics, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the diuretics may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The diuretics of the invention can be administered in such oral forms as tablets, capsules and granules. The diuretics are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

METHODS OF SYNTHESIS

Several methods for preparing the compounds of this invention are described in the following Schemes and Examples. Starting materials and intermediates are made from known procedures or as otherwise illustrated. Unless otherwise noted, variables are as defined above.

Scheme 1 describes a convenient method to prepare 3-(4-chlorophenyl)-6-methyl-1,3-dihydrofuro[3,4-c]pyridin-7-yl carboxylate ester compounds of the general structure 1-3 in this invention. Either racemic or enantiomeric phenol 1-1 is treated with an activated acid 1-2 at an appropriate temperature such as room temperature in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. Acid chloride 1-2 can be readily formed by treating an appropriate carboxylic acid with a chlorinating reagent such as thionyl chloride, phosphorus trichloride, phosphorus pentachloride, oxalyl chloride in the presence of catalytical amount of Vilsmeier reagent, or triphenylphosphine and carbon tetrachloride or trichloroacetonitrile. Other forms of activated acid 1-2 can be prepared using methods known to those skilled in the art.

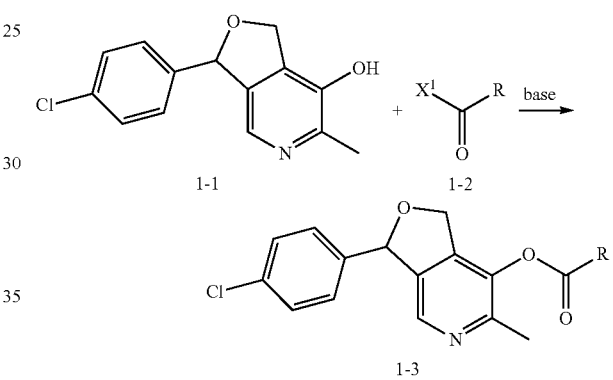

Scheme 1

$X^1$ = Cl, Br, F, $OC_6F_5$, N-hydroxysuccinimide

Scheme 2 delineates an alternative method to prepared 3-(4-chlorophenyl)-6-methyl-1,3-dihydrofuro[3,4-c]pyridin-7-yl carboxylate ester compounds of the general structure 1-3 in this invention. The carboxylic acid in this reaction can be activated for acylation at an appropriate temperature such as room temperature with a suitable coupling reagent such as N,N-dicyclohexylcarbodiimide (DCC), 1-(3-dimethylaminopropyl)-3-ethylcarbodiimide (EDC), (benzotriazol-1-yl-oxy)tripyrrolidinophosphonium hexafluorophosphate (PyBOP), bis(2-oxo-3-oxazolidinyl)phosphinic chloride (BOP-Cl), or 1,1'-carbonyldiimidazole in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or methylpyrrolidinone.

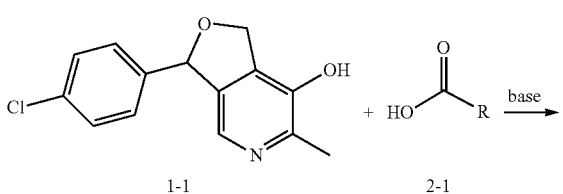

Scheme 2

-continued

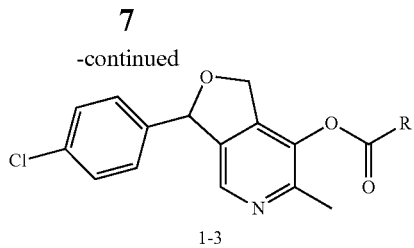

1-3

Scheme 3 describes a straightforward method to prepare 3-(4-chlorophenyl)-6-methyl-1,3-dihydrofuro[3,4-c]pyridin-7-yl carbonate compounds of the general structure 3-2 in this invention. Either racemic or enantiomeric phenol 1-1 is treated with an activated formate 3-1 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated formate 3-1 can be prepared by treating an appropriate alcohol at an appropriate temperature such as 0° C. or room temperature with a suitable reagent such as phosgene, trichloromethyl chloroformate, 1,1'-carbonyldiimidazole, p-nitrophenyl chloroformate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 3

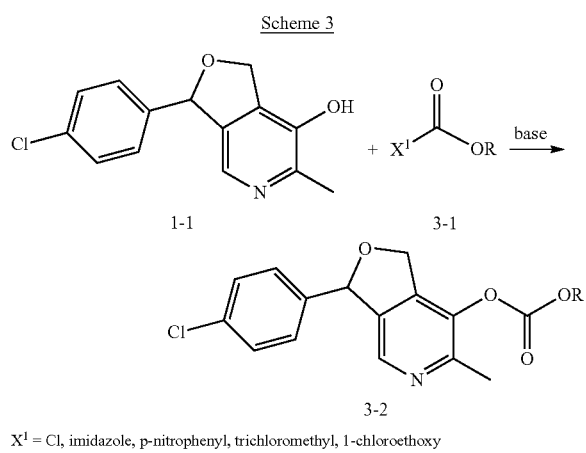

$X^1$ = Cl, imidazole, p-nitrophenyl, trichloromethyl, 1-chloroethoxy

Finally, Scheme 4 describes an alternative method to prepare 3-(4-chlorophenyl)-6-methyl-1,3-dihydrofuro[3,4-c] pyridin-7-yl carbonate compounds of the general structure 3-2 in this invention. In this reaction, an activated formate 4-1 of either racemic or enantiomeric 3-(4-chlorophenyl)-6-methyl-1,3-dihydrofuro[3,4-c]pyridin-7-ol is treated with an appropriate alcohol 4-2 at an appropriate temperature such as room temperature in the presence of a suitable base such as N,N-diisopropylethylamine, triethylamine, N-methylmorpholine, pyridine, lutidine, potassium carbonate, sodium carbonate, cesium carbonate, or sodium hydride in an appropriate solvent such as dichloromethane, dichloroethane, chloroform, acetonitrile, tetrahydrofuran, dioxane, toluene, N,N-dimethylformamide, or N-methylpyrrolidinone. The activated formate 4-1 can be prepared by treating the phenol 1-1 at an appropriate temperature such as 0° C. or room temperature with a suitable reagent such as phosgene, trichloromethyl chloroformate, 1,1'-carbonyldiimidazole, p-nitrophenyl chloroformate, trichloroacetyl chloride, or 1-chloroethyl chloroformate in the presence of a suitable base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone.

Scheme 4

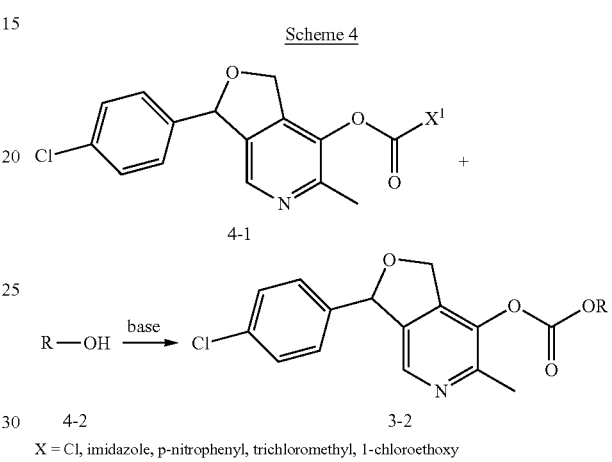

X = Cl, imidazole, p-nitrophenyl, trichloromethyl, 1-chloroethoxy

General Procedures.

Reactions sensitive to moisture or air were performed under nitrogen or argon using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 2.1×20 mm column with gradient 10:90-98:2 v/v $CH_3CN/H_2O$+v 0.05% TFA over 3.25 min then hold at 98:2 v/v $CH_3CN/H_2O$+v 0.05% TPA for 0.75 min; flow rate 1.5 mL/min, UV wavelength 254 nm. Two other HPLC conditions applied were noted as LC-1 (Waters C18 XTerra 3.5 μm 2.1×20 mm column with gradient 10:90-98:2 v/v $CH_3CN/H_2O$+v 0.05% TFA over 1.25 min then hold at 98:2 v/v $CH_3CN/H_2O$+v 0.05% TFA for 0.75 min; flow rate 1.5 mL/min, UV wavelength 254 nm) and LC-2 (Waters C18 XTerra 3.5 μm 30×50 mm column with gradient 10:90-98:2 v/v $CH_3CN/H_2O$+v 0.05% TEA over 3.75 min then hold at 98:2 v/v $CH_3CN/H_2O$+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) or a CombiFlash Rf apparatus (Teledyne ISCO) on silica gel (32-63 μM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $\underline{CH_3OH}$ peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, or Chiralcel OJ columns (20×250 mm) (Daicel Chemical Industries, Ltd.) with desired isocratic solvent systems identified on chiral analytical chromatography.

Abbreviations: acetic acid (AcOH), aqueous (aq), (benzotriazol-1-yloxy)tripyrrolidino-phosphonium hexafluorophosphate (PyBOP), 2,2'-bis(diphenylphosphino)-1,1'-binaphthalene (BINAP), 1,1'-bis(diphenylphosphino) ferrocene (dppf), 4-N,N-dimethylaminopyridine (DMAP), ethyl acetate (EtOAc), diethyl ether (ether or Et$_2$O), N,N-diisopropylethylamine (DIEA), N,N-dimethylformamide (DMF), gram(s) (g), hour(s) (h or hr), microliter(s) (µL), milligram(s) (mg), milliliter(s) (mL), millimole (mmol), mass spectrum (ms or MS), 2-propanol (IPA), retention time (R$_t$), room temperature (rt), saturated aq sodium chloride solution (brine), trifluoroacetic acid (TFA), tetrahydrofuran (THF), and minute(s) (min).

EXAMPLE 1

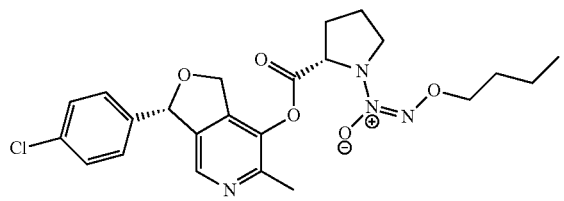 [SMILES: CCCCO/N=[N+](/[O-])N1CCC[C@H]1C(=O)Oc1c(C)ncc2c1CO[C@H]2c1ccc(Cl)cc1]

(3S)-3-(4-Chlorophenyl)-6-methyl-1,3-dihydrofuro[3,4-c]pyridin-7-yl 1-[(Z)-butoxy-NNO-azoxy]-L-prolinate Step A: {(2S)-1-[(Z)-1-butoxy-NNO-azoxy]pyrrolidin-2-yl}methanol To a suspension of sodium (2S)-2-(hydroxymethyl)-1-[(Z)-oxido-NNO-azoxy]pyrrolidine (447 mg, 2.44 mmol) and tetrabutylammonium iodide (90 mg, 0.24 mmol) in DMF (10 mL) was added 1-bromobutane (315 µL, 2.93 mmol). The resulting suspension was allowed to stir at 65° C. over night. After cooling to rt, the mixture was partitioned between Et$_2$O (50 mL) and brine (50 mL). The organic layer was separated and washed with brine (2×50 mL), dried over MgSO$_4$ and concentrated. The residue was purified by flash chromatography (Biotage 40+M) using 35-50% ethyl acetate in hexanes gradient, affording the title product: $^1$H NMR (500 MHz, CDCl$_3$) δ 4.21 (t, J=6.7 Hz, 2H), 4.07-4.02 (m, 1H), 3.75 (dd, J=3.6, 11.3 Hz, 1H), 3.63-3.54 (m, 3H), 3.06 (br. s, 1H), 2.12-2.04 (m, 1H), 1.98-1.91 (m, 2H), 1.81-1.71 (m, 3H), 1.47-1.39 (m, 2H), 0.95 (t, J=7.4 Hz, 3H).

Step B: 1-[(Z)-butoxy-NNO-azoxy]-L-proline

To a solution of {(2S)-1-[(Z)-1-butoxy-NNO-azoxy]pyrrolidin-2-yl}methanol (360 mg, 1.66 mmol) and sodium periodate (1.06 g, 4.97 mmol) in 17.5 mL of CH$_3$CN/CCl$_4$/H$_2$O (2:2:3) was added ruthenium(III) chloride hydrate (34 mg, 1.66 mmol). After stirring at rt over night, the mixture was extracted with CH$_2$Cl$_2$ (3×50 mL), dried over MgSO$_4$ and concentrated to give the title product, which was used directly.

Step C: (3S)-3-(4-chlorophenyl)-6-methyl-1,3-dihydrofuro[3,4-c]pyridin-7-yl 1-[(Z)-butoxy-NNO-azoxy]-L-prolinate To a solution of (3S)-3-(4-chlorophenyl)-6-methyl-1,3-dihydrofuro[3,4-c]pyridine-7-ol (346 mg, 1.32 mmol), 1-[(Z)-butoxy-NNO-azoxy]-L-proline (306 mg, 1.32 mmol), and triethylamine (369 mL, 2.65 mmol) in CH$_2$Cl$_2$ (10 mL) was added BOP-Cl (438 mg, 1.72 mmol). After stirring at rt over night, the mixture was purified by flash chromatography (Biotage 40+M) using 40-50% EtOAc/hexane gradient, affording the title compound: $^1$H NMR (500 MHz, CDCl$_3$) δ 8.05 (s, 1H), 7.35-7.33 (m, 2H), 7.28-7.25 (m, 2H), 6.19 (s, 1H), 5.21 (dd, J=2.4, 14.1 Hz, 1H), 5.07 (dd, J=1.9, 14.2 Hz, 1H), 4.78 (dd, J=4.5, 14.1 Hz, 1H), 4.20 (t, 6.7 Hz, 2H), 3.93-3.88 (m, 1H), 3.73-3.68 (m, 1H), 2.54-2.48 (m, 1H), 2.47 (s, 3H), 2.26-2.15 (m, 3H), 1.76-1.70 (m, 2H), 1.45-1.38 (m, 2H), 0.93 (t, J=7.4 Hz, 3H).

EXAMPLES 2-11

The following examples were prepared using procedures analogous to those described for EXAMPLE 1 substituting appropriate alkyl halides or alkyl mesylates for 1-bromobutane in Step A.

| Example | R | HPLC R$_t$ (min) | MS (M + H) |
|---|---|---|---|
| 2 | ⸺CH$_3$ | 1.76 | 433.2 |
| 3 | ⸺CH$_2$CH$_3$ | 1.86 | 447.3 |
| 4 | ⸺CH(CH$_3$)$_2$ | 1.95 | 461.3 |
| 5 | ⸺CH$_2$CH(CH$_3$)$_2$ | 2.09 | 475.3 |
| 6 | ⸺CH$_2$CH$_2$CH$_3$ | 1.99 | 461.4 |

-continued

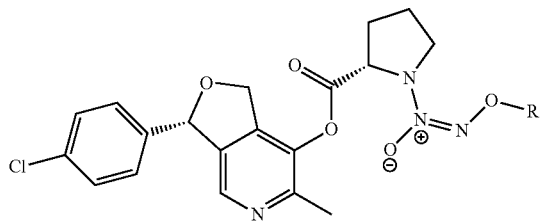

| Example | R | HPLC R$_t$ (min) | MS (M + H) |
|---|---|---|---|
| 7 | ⁓⁓⁓CH$_2$CH$_2$CH$_2$CH$_2$CH$_3$ | 2.21 | 489.4 |
| 8 | ⁓⁓⁓CH$_2$CH$_2$CH(CH$_3$)$_2$ | 2.19 | 489.4 |
| 9 | ⁓⁓⁓CH(CH$_3$)CH$_2$CH$_3$ | 2.32 | 489.4 |
| 10 | ⁓⁓⁓CH$_2$C*H(CH$_3$)CH$_2$CH$_3$ | 2.19 | 489.38 |
| 11 | ⁓⁓⁓CH$_2$-cyclohexyl | 3.51 | 501.08 |

EXAMPLE 12

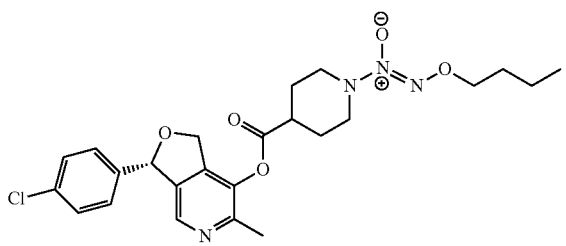 [SMILES: CCCCO/N=[N+](\[O-])N1CCC(C(=O)Oc2c(C)ncc3c2CO[C@H]3c2ccc(Cl)cc2)CC1]

(3S)-3-(4-Chlorophenyl)-6-methyl-1,3-dihydrofuro[3,4-c]pyridin-7-yl 1-[(Z)-butoxy-NNO-azoxy]piperidine-4-carboxylate Step A: {1-[(E)-1-butoxy-NNO-azoxy]piperidin-4-yl}methanol A suspension of sodium (2S)-2-(hydroxymethyl)-1-[(Z)-oxido-NNO-azoxy]piperidine (1.04 g, 5.27 mmol) and 1-bromobutane (681 μL, 6.33 mmol) in DMF (5 mL) was stirred at 100° C. for 30 min in a microwave reactor. After cooling to rt, the mixture was partitioned between Et$_2$O (50 mL) and brine (50 mL). The organic layer was separated and washed with brine (2×50 mL), dried over MgSO$_4$ and concentrated. The residue was purified by flash chromatography (Biotage 40+M) using 40-50% EtOAc in hexanes gradient, affording the title product: $^1$H NMR (500 MHz, CDCl$_3$) δ 4.23 (t, 6.9 Hz, 2H), 3.82-3.78 (m, 2H), 3.53 (d, J=6.4, Hz, 2H), 2.95 (dt, J=2.5, 11.9 Hz, 2H), 1.90 (d, J=7.1 Hz, 2H), 1.77-1.71 (m, 2H), 1.65 (m, 2H), 1.50-1.40 (m, 4H), 0.94 (t, J=7.5 Hz, 3H).

Step B: (3S)-3-(4-chlorophenyl)-6-methyl-1,3-dihydrofuro[3,4-c]pyridin-7-yl 1-[(Z)-butoxy-NNO-azoxy]piperidine-4-carboxylate The title compound was prepared using procedures analogous to those described for EXAMPLE 1 substituting {1-[(E)-1-butoxy-NNO-azoxy]piperidin-4-yl}methanol for {(2S)-1-[(Z)-1-butoxy-NNO-azoxy]pyrrolidin-2-yl}methanol in Step B: $^1$H NMR (500 MHz, CDCl$_3$) δ 8.07 (s, 1H), 7.35 (d, J=8.4 Hz, 2H), 7.27 (d, J=82 Hz, 2H), 6.20 (s, 1H), 5.12 (dd, J=2.3, 13.7 Hz, 1H), 5.02 (dd, J=1.8, 13.7 Hz, 1H), 4.25 (t, J=6.9 Hz, 2H), 3.81-3.85 (m, 2H), 3.17 (dt, J=2.8, 11.5 Hz, 2H), 2.74-2.81 (m, 1H), 2.44 (s, 3H), 2.28-2.24 (m, 2H), 2.17-2.09 (m, 2H), 1.78-1.72 (m, 2H), 1.45-1.39 (m, 2H), 0.95 (t, J=7.3 Hz, 3H).

EXAMPLE 13

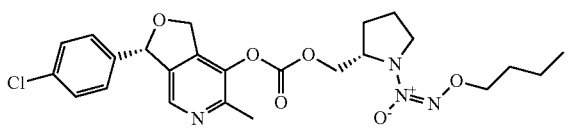 [SMILES: CCCCO/N=[N+](/[O-])N1CCC[C@H]1COC(=O)Oc1c(C)ncc2c1CO[C@H]2c1ccc(Cl)cc1]

{(2S)-1-[(E)-butoxy-NNO-azoxy]pyrrolidin-2-yl}methyl(3S)-3-(4-chlorophenyl)-6-methyl-1,3-dihydrofuro[3,4-c]pyridin-7-yl carbonate Step A: {(2S)-1-[(Z)-butoxy-NNO-azoxy]pyrrolidin-2-yl}methyl 1-chloroethyl carbonate To a solution of {(2S)-1-[(2)-butoxy-NNO-azoxy]pyrrolidin-2-yl}methanol (Example 1, Step A) (856 mg, 3.94 mmol) in CH$_2$Cl$_2$ (15 mL) at rt was added 1-chloroethyl chloroformate (676 mg, 4.73 mmol) and followed by pyridine (935 mg, 11.8 mmol). After stirring at rt for 3 h, the mixture was purified by flash chromatography (Biotage 25+M) using 10-30% EtOAc/hexane gradient, affording the title compound.

Step B: {(2S)-1-[(E)-butoxy-NNO-azoxy]pyrrolidin-2-yl}methyl(3S)-3-(4-chlorophenyl)-6-methyl-1,3-dihydrofuro[3,4-c]pyridin-7-yl carbonate To a solution of (3S)-3-(4-chlorophenyl)-6-methyl-1,3-dihydrofuro[3,4-c]pyridine-7-ol (900 mg, 3.44 mmol) in DMF (10 mL) at 0° C. was added sodium hydride (206 mg, 5.16 mmol) and, in 10 minutes, followed by addition of {(2S)-1-[(Z)-butoxy-NNO-azoxy]pyrrolidin-2-yl}methyl 1-chloroethyl carbonate (1.3 g, 4.02 mmol). After stirring at rt for 3 h, the mixture was partitioned between Et$_2$O (50 mL) and water (50 mL). The organic layer was washed with brine (3×50 mL), dried over MgSO$_4$, and concentrated. The residue was purified by flash chromatography (Biotage 25+M) using 30-50% EtOAc/hexane gradient, affording the title compound: ¹H NMR (500 MHz, CDCl₃) δ 8.08 (s, 1H), 7.37-7.27 (m, 4H), 6.21 (s, 1H), 5.29-5.13 (m, 2H), 4.49 (m, 1H), 4.40 (m, 1H), 4.35 (m, 1H), 4.20 (m, 2H), 3.65 (m, 1H), 3.57 (m, 1H), 2.52 (s, 3H), 2.20 (m, 1H), 2.05 (m, 2H), 1.90 (m, 1H), 1.75 (m, 2H), 1.42 (m, 2H), 0.94 (m, 3H).

EXAMPLE 14

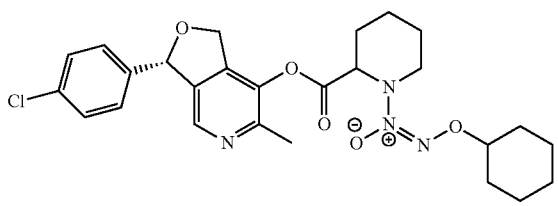 [SMILES: Cc1ncc2c(c1OC(=O)C1CCCCN1/[N+]([O-])=N\OC1CCCCC1)CO[C@H]2c1ccc(Cl)cc1]

(3S)-3-(4-chlorophenyl)-6-methyl-1,3-dihydrofuro[3,4-c]pyridin-7-yl 1-[(E)-(cyclohexyloxy)-NNO-azoxy]piperidine-2-carboxylate The title compound was made by following the procedures described in EXAMPLE 1 substituting sodium 2-(hydroxymethyl)-1-[(Z)-oxido-NNO-azoxy]piperidine for sodium (2S)-2-(hydroxymethyl)-1-[(Z)-oxido-NNO-azoxy]pyrrolidine and iodohexane for 1-bromobutane in step A. The two diastereomers were separated by normal phase preparative chiral HPLC (Chiralcel OD), eluting with 30% ethanol in heptane. Diastereomer A: ¹H NMR (500 MHz, CDCl₃) δ 8.05 (1H, s), 7.34 (2H, d, J=8.3 Hz), 7.25 (2H, d, J=8.3 Hz), 6.18 (1H, s), 5.14 (1H, dd, J=14.0, 2.4 Hz), 5.03 (1H, dd, J=14.0, 1.8 Hz), 4.65 (1H, dd, J=8.1, 4.3 Hz), 4.28-4.20 (1H, m), 3.72 (1H, ddd, J=11.0, 6.8, 3.9 Hz), 3.58 (1H, ddd, J=10.9, 8.4, 3.7 Hz), 2.45 (3H, s), 2.30-2.22 (1H, m), 2.21-2.12 (1H, m), 2.01-1.87 (3H, m), 1.88-1.67 (4H, m), 1.67-1.48 (4H, m), 1.38-1.16 (3H, m). Diastereomer B: ¹H NMR (500 MHz, CDCl₃) δ 8.04 (1H, s), 7.34 (2H, d, J=8.4 Hz), 7.26 (2H, d, J=7.7 Hz), 6.18 (1H, s), 5.17 (1H, dd, J=14.1, 2.5 Hz), 5.00 (1H, dd, J=14.1, 1.9 Hz), 4.64 (1H, dd, J=8.1, 4.3 Hz), 4.27-4.20 (1H, m), 3.73 (1H, ddd, J=10.9, 6.7, 3.9 Hz), 3.57 (1H, ddd, J=10.9, 8.4, 3.7 Hz), 2.44 (3H, s), 2.29-2.23 (1H, m), 2.20-2.13 (1H, m), 2.01-1.88 (3H, m), 1.89-1.65 (4H, m), 1.66-1.50 (4H, m), 1.36-120 (3H, m).

Compounds of the invention were evaluated for blood pressure reduction efficacy using the following canine telemetry protocol.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| Compound | ΔSBP (mm Hg) | | | ΔPP (mm Hg) | | |
| --- | --- | --- | --- | --- | --- | --- |
| | 1-6 h | 6-12 h | 12-18 h | 1-6 h | 6-12 h | 12-18 h |
| 1 | −15.4 | −6.2 | −0.6 | −14.0 | −6.4 | −3.2 |
| 5 | −2.4 | −2.6 | −2.8 | −3.6 | −1.7 | −2.6 |
| 9 | −11.8 | −6.6 | 1.0 | −10.6 | −5.2 | −2.5 |
| 10 | −5.3 | −0.9 | −3.1 | 0.6 | 3.4 | 3.8 |
| 11 | −9.3 | −3.3 | 3.9 | −6.9 | −2.3 | 0.9 |
| 12 | −11 | −5.8 | 3.3 | −12 | −5.8 | 0.8 |

What is claimed is:

1. A compound of the formula I:

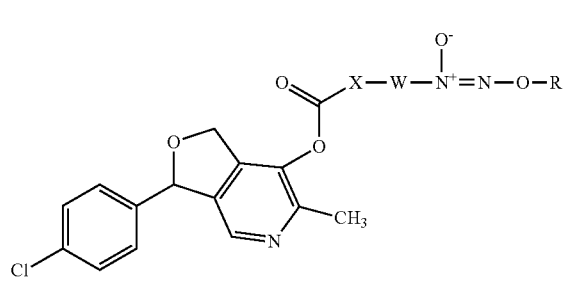

wherein

X is a bond or —O—C₁₋₆alkylene-, wherein C₁₋₆ alkylene is unsubstituted, mono-substituted at any carbon with C₁₋₆ alkyl, or independently disubstituted at different carbons with C₁₋₆ alkyl;

W is selected from the group consisting of

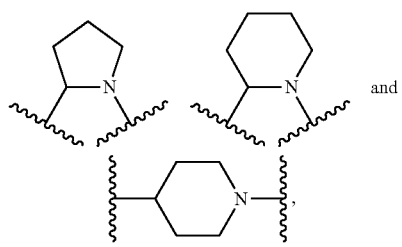

wherein N is attached to

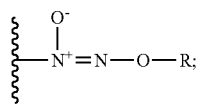

and

R is selected form the group consisting of $C_{1-6}$ alkyl and $C_{3-6}$ cycloalkyl, or a pharmaceutically acceptable salt thereof.

2. A compound of claim 1, wherein X is a bond or —OCH$_2$—, or a pharmaceutically acceptable salt thereof.

3. A compound of claim 1, wherein R is selected from the group consisting of methyl, ethyl, propyl, isopropyl, 2-methylpropyl, butyl, 3-methylbutyl, pentyl and pentan-2-yl, or a pharmaceutically acceptable salt thereof.

4. A compound of claim 1, selected from the group consisting of (3S)-3-(4-Chlorophenyl)-6-methyl-1,3-dihydrofuro[3,4-c]pyridin-7-yl 1-[(Z)-butoxy-NNO-azoxy]-L-prolinate, (3S)-3-(4-Chlorophenyl)-6-methyl-1,3-dihydrofuro[3,4-c]pyridin-7-yl 1-[(Z)-methoxy-NNO-azoxy]-L-prolinate, (3S)-3-(4-Chlorophenyl)-6-methyl-1,3-dihydrofuro[3,4-c]pyridin-7-yl 1-[(Z)-ethoxy-NNO-azoxy]-L-prolinate, (3S)-3-(4-Chlorophenyl)-6-methyl-1,3-dihydrofuro[3,4-c]pyridin-7-yl 1-[(Z)-isopropyloxy-NNO-azoxy]-L-prolinate, (3S)-3-(4-Chlorophenyl)-6-methyl-1,3-dihydrofuro[3,4-c]pyridin-7-yl 1-[(Z)-2-methylpropoxy-NNO-azoxy]-L-prolinate, (3S)-3-(4-Chlorophenyl)-6-methyl-1,3-dihydrofuro[3,4-c]pyridin-7-yl 1-[(Z)-propoxy-NNO-azoxy]-L-prolinate, (3S)-3-(4-Chlorophenyl)-6-methyl-1,3-dihydrofuro[3,4-c]pyridin-7-yl 1-[(Z)-pentoxy-NNO-azoxy]-L-prolinate, (3S)-3-(4-Chlorophenyl)-6-methyl-1,3-dihydrofuro[3,4-c]pyridin-7-yl 1-[(Z)-3-methylbutoxy-NNO-azoxy]-L-prolinate, (3S)-3-(4-Chlorophenyl)-6-methyl-1,3-dihydrofuro[3,4-c]pyridin-7-yl 1-[(Z)-pentan-2-yloxy-NNO-azoxy]-L-prolinate, (3S)-3-(4-Chlorophenyl)-6-methyl-1,3-dihydrofuro[3,4-c]pyridin-7-yl 1-((Z)-{[(2S)-2-methylbutyl]oxy}-NNO-azoxy)-L-prolinate, (3S)-3-(4-Chlorophenyl)-6-methyl-1,3-dihydrofuro[3,4-c]pyridin-7-yl 1-[(Z)-cyclohexyloxy-NNO-azoxy]-L-prolinate, (3S)-3-(4-Chlorophenyl)-6-methyl-1,3-dihydrofuro[3,4-c]pyridin-7-yl 1-[(Z)-butoxy-NNO-azoxy]piperidine-4-carboxylate, {(2S)-1-[(E)-butoxy-NNO-azoxy]pyrrolidin-2-yl}methyl (3S)-3-(4-chlorophenyl)-6-methyl-1,3-dihydrofuro[3,4-c]pyridin-7-yl carbonate, and (3S)-3-(4-chlorophenyl)-6-methyl-1,3-dihydrofuro[3,4-c]pyridin-7-yl 1-[(E)-(cyclohexyloxy)-NNO-azoxy]piperidine-2-carboxylate or a pharmaceutically acceptable salt thereof.

5. A pharmaceutical composition comprising a compound of claim 4 and a pharmaceutically acceptable carrier.

6. A pharmaceutical composition comprising a compound of claim 1 and a pharmaceutically acceptable carrier.

7. A pharmaceutical composition comprising a compound of claim 1, a diuretic, and a pharmaceutically acceptable carrier.

8. A method for treating hypertension in a patient which comprises administering to the patient a therapeutically effective amount of the composition of claim 5.

\* \* \* \* \*